United States Patent [19]

Vogel

[11] Patent Number: 4,787,373

[45] Date of Patent: Nov. 29, 1988

[54] FACIAL IRONER

[76] Inventor: Peter Vogel, 125 Auburn Ct., Ste. 200, Westlake Village, Calif. 91361

[21] Appl. No.: 62,017

[22] Filed: Jun. 15, 1987

[51] Int. Cl.[4] ............................................. A61H 21/00
[52] U.S. Cl. .................................... 128/24.1; 128/362; 128/399
[58] Field of Search ..................... 128/24.1, 24.5, 24.2, 128/44, 67, 399, 400, 362, 355, 303.1, 355; 126/230, 227, 228

[56]  References Cited

U.S. PATENT DOCUMENTS

| 1,597,732 | 8/1926 | Shanly | 128/24.1 |
| 2,231,095 | 2/1941 | Sommer et al. | 128/24.1 |
| 2,593,875 | 4/1952 | Grunwald | 128/24.2 |
| 2,698,617 | 1/1955 | Simmons | 128/24.1 |
| 2,809,630 | 10/1957 | Volker | 128/24.3 |
| 4,090,517 | 5/1978 | Nagatoki | 128/399 |
| 4,291,685 | 9/1981 | Taelman | 128/32 |

FOREIGN PATENT DOCUMENTS 2340742  9/1977  France .................................. 128/24.1

Primary Examiner—David A. Wiecking
Assistant Examiner—Huong Q. Pham
Attorney, Agent, or Firm—Richard D. Slehofer

[57] ABSTRACT

A facial ironer is disclosed for heating a subject's skin after an emollient has been previously applied. The ironer is demountable attached to a heating element contained within a housing. The ironer includes a triangular-shaped soleplate having a butted slotted end for slipping over the heating element. Heat is transferred from the heating element to the metallic soleplate. The soleplate has an insulated gripper for holding and manipulating the heated surface of the soleplate over the subject's face for heating the emollient and for providing a facial treatment to the subject.

7 Claims, 2 Drawing Sheets

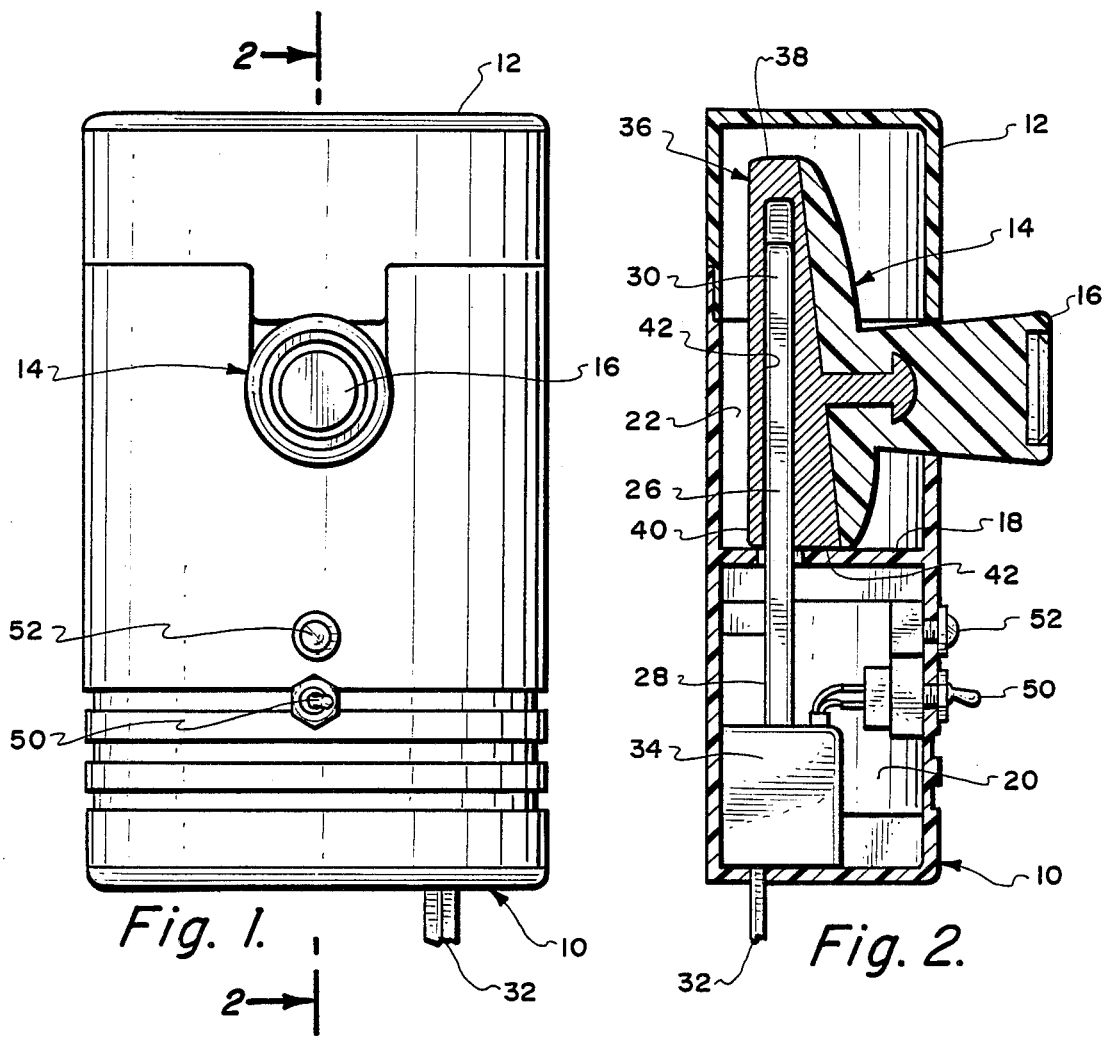
Fig. 1.
Fig. 2.
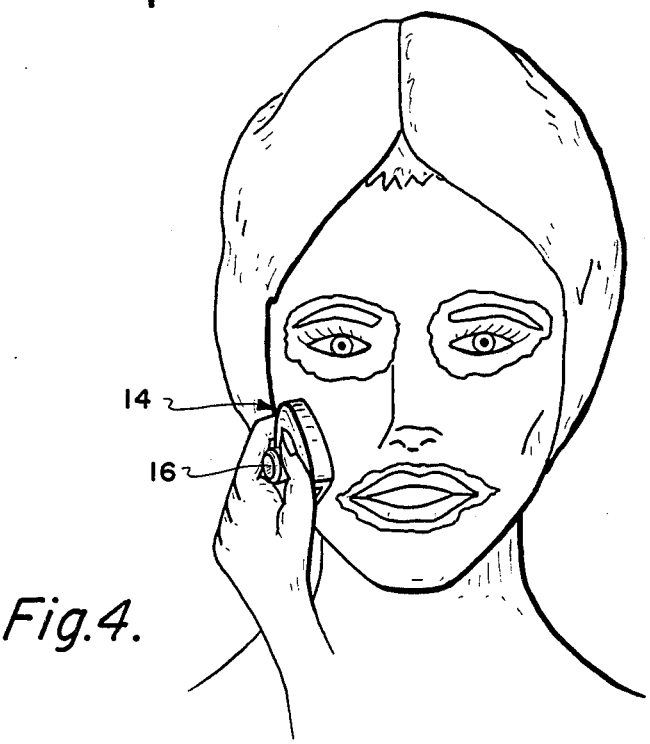
Fig. 4.

FACIAL IRONER

BACKGROUND OF THE INVENTION

1. Field of the Invention

The present invention pertains to surgery and in particular to a dermatological device for applying thermal heat to the subject's skin on the head, face and neck.

2. Description of the Prior Art

Taelman, U.S. Pat. No. 4,291,685 discloses a portable, hand held applicator permanently connected to an electrical cord. There is a heating rheostat for adjusting the current flow into the applicator's heating head. The heating head includes openings for allowing the seepage of liquid from the hollow handle and onto the skin surface. There is also a means for vibrating the handle. The heating head is detachable.

It is also known in the art a skin ironer which is molded from a clear plastic material forming a large reservoir head at one end and having a round extension for forming a handle having a stoppered end. Heated oil is poured into the cavity or reservoir forming the ironer and the rubber stopper is inserted to keep the oil from leaking out. The heated oil heats up the molded plastic ironer's head which is then passed over cosmetic material previously applied to the face, thereby warming the cosmetic material for penetrating the underlying facial skin.

SUMMARY OF THE INVENTION

The facial ironer apparatus is intended to be used in the area of cosmetics. It is used as a commercial or home facial treatment to help cleanse, smooth, rejuvenate, soften and press out wrinkles on the skin. Various types of dermatological salves and ingredients can be initially applied to the facial area. After the facial ironer has been heated to its working temperature, the facial ironer is manipulated over the skin area to warm the material previously applied so that the transferred heat will cause more penetration of the cream or other applied materials into the epidermis. The facial ironer apparatus includes a housing which holds a heating element having a base and a head. There is an electrical cord connecting the apparatus to a conventional AC electrical cord outlet. There is a thermostatic switch in the housing which interconnects the electrical cord and the base of the heating element for maintaining the temperature of the heating element at a predetermining setting. The facial ironer itself is demountably attached to the head of the heating element. The facial ironer includes a triangular-shaped soleplate which has a bottom and a slotted butted end. The soleplate itself is relatively thick and sufficiently hollow for closely fitting over the head of the heating element by entering it through the slotted end. The soleplate is heated by the transfer of heat from the heating element which has been heated by the flow of electricity from the electrical outlet. The soleplate could be fabricated from a metal. There is also a handle for attachment to the top of the soleplate for holding and manipulating the facial ironer as the bottom of the ironer is passed over the skin of the subject. The soleplate of the facial ironer can get no hotter than the temperature of the heating element. The temperature of the heating element is in turn controlled by a thermostatic switch which is preset at the factory to maintain the soleplate temperature at around 95 degree F temperature. There can also be included an indicator light for indicating when the soleplate has reached the predetermined operating temperature.

In operation, the user passes the facial ironer over the skin until the ironer dissipates its heat. The ironer is then reattached to the heating element to allow the soleplate to absorb heat until it reaches operating temperature again. This process is repeated until the entire facial area of the subject has been thoroughly heated and the applied cream has penetrated sufficiently.

BRIEF DESCRIPTION OF THE DRAWINGS

FIG. 1 is a front elevational view illustrating the housing and cover of the device.

FIG. 2 is a vertical cross-sectional view taken along the lines 2—2 of FIG. 1 illustrating how the soleplate of the facial ironer cooperates with the heating element.

FIG. 4 illustrates the operation of the facial ironer and the size of the ironer relative to the user. As can be seen, the skin surface has already been prepared with the appropriate type of facial cream and then the ironer is passed over this area for heating up and penetrating the applied substance.

DETAILED DESCRIPTION OF THE PREFERRED EMBODIMENT

Figure 3:
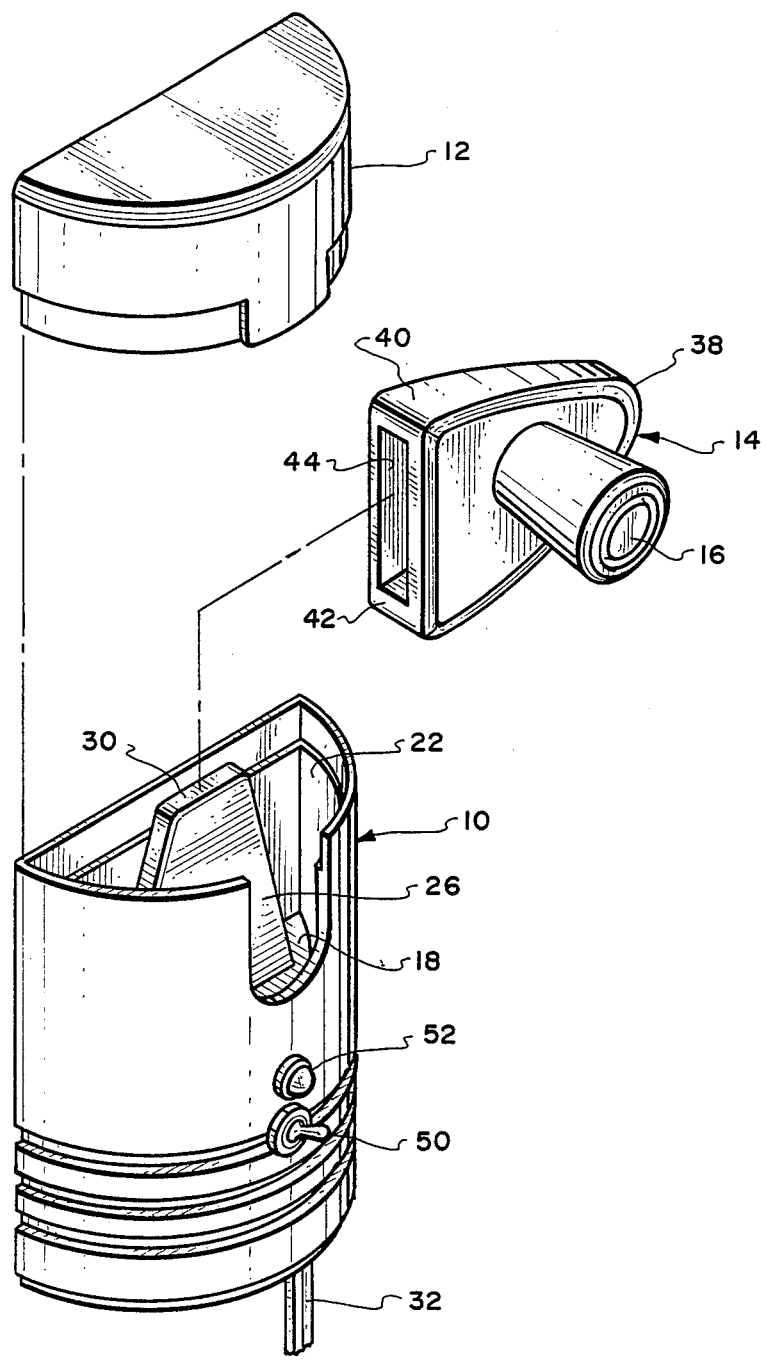
FIG. 3 is an exploded prospective view showing the three basic components comprising the invention.

Referring now to FIG. 1, there is disclosed the front elevational view of the device showing the overall housing 10, the cap or cover 12 and the handle 16 which extends from the facial ironer 14 which is only partially shown in this view.

Referring to FIG. 2, which is a longitudinal cross-sectional view taken along the lines 2—2 of FIG. 1, there is clearly shown the facial ironer labeled overall as 14. The handle 16 is also shown in this view. The housing 10 includes a partition 18 which forms a first compartment 20 and a second compartment 22. There is an elongate heating element 26 having a base 28 and a tapered head 30 which is positioned lengthwise within the housing 10 and extending from either side of the partition 18 into both compartments 20 and 22. There is an electrical cord 32 which connects the overall device to a source of electricity such as an AC outlet. Also illustrated in FIG. 2 is a thermostatic switch means 34 positioned in the first compartment 20 and interconnecting the electrical outlet cord means 32 and the base of the heating element 28 for maintaining the heating element at a predetermining temperature. The thermostatic switch means is illustrated as a thermostatic switch. A rheostat could be substituted for the thermostatic switch to allow the operator to adjust the temperature of the soleplate.

The facial ironer 14 is demountably attached to the head 30 of the heating element 26. The facial ironer 14 includes a blunt wedge shaped metallic soleplate 36 which has a top 38, a bottom 40 and a butted end 42. The butted end 42 further includes a receiving slot 44. The soleplate 36 is sufficiently hollow for closely fitting over the head 30 of the heating element 26. This is clearly shown in FIG. 2. The purpose of this soleplate being sufficiently hollow is to allow it to closely fit over the head of the heating element through the slot while the butted end of the facial ironer rests on the partition 18. The resting position on the head is shown in FIG. 2. The soleplate is heated by conductive heat transferred from the heating element when the heating element is heated by the flow of electricity from the cord. There is an insulated handle for attachment to the top of the soleplate for use in manipulating the bottom of the facial ironer over the prepared surface of the face area of the subject. The insulated handle means is illustrated as a gripper or handle 16.

FIG. 3 shows how the facial ironer is adapted for closely fitting over the tapered head of the heating element and also illustrates the partition over which the butt rests against when the ironer is not in use or is being reheated. The partition, of course, is not critical to the use of this invention, because the tapered head of the heating element could by itself hold the facial ironer in position without the need for the partition. The cover means 12 is illustrated as a cover for covering the second compartment and for securing the facial ironer when it is attached to the element head. There is a slot cut away from the face of the housing which allows the handle 16 to be cradled. The cover 12, when in position, prevents the facial ironer from disengaging from the heating element. Further features shown in FIG. 3 include an on and off switch 50 and a light indicator means 52 for indicating when the heating element is at its predetermining temperature. The light indicator means is illustrated as a red light 52. The on/off switch 50 avoids having to disconnect the plug whenever the device is not in use. It is simply a convenience feature.

OPERATION OF THE INVENTION

FIG. 4 illustrates an example of how the device can be used. It is one form of facial treatment. The skin surface is prepared beforehand by washing the skin surface to remove any accumulated dirt or cosmetic material. The next step is to apply the appropriate formulations to the skin recommended for a particular facial treatment. There are a variety of skin creams available such as collagen, elastin and other generic types of formulations for skin which will deeply cleanse the skin, soften out the wrinkles, increase the rosy appearance of the skin and the like. It is up to the individual user or cosmetologist to make the determination on the appropriate surface formulation to be applied to the subject. During the application of the skin cream, the facial ironer is attached to the heating element and the facial ironer device is energized by either plugging in the device or turning on the on/off switch. After a short period of time the red light energizes to indicate that the soleplate of the facial ironer has reached the operating temperature of 96 degrees F. The handle 14 is gripped by the hand and the soleplate of the facial ironer is manipulated over the skin area where the cream has been previously applied. A sufficient amount of time is required to heat the skin cream and have it penetrate the pores of the skin as it was intended to do. Obviously the heat from the soleplate of the facial ironer is dissipated by the cream and the face. Therefore, the operator has to replace the soleplate on the tapered head to reheat the soleplate once again to its operating temperature. This process is repeated until the applied cream has been heated sufficiently. Afterwards, the facial ironer is turned off and the facial cream is removed.

It is not intended that this application be limited to heating facial creams on the face of a subject. It could be adaptable to any surface area such as the sole of the feet or areas where roughness of the skin is present and where it would be beneficial to treat the area with an emollient and have the ironer heat and penetrate the lotion upon the feet area, the kneecap area, the elbow area or any other part of the body where heating and penetration of an applied substance would be thought to be beneficial to the skin.

While the present invention has been shown and described herein in what is conceived to be the best mode contemplated, it is to be recognized that departures may be made therefrom within the scope of the invention which is therefore not to be limited to the details disclosed herein, but is to be afforded the full scope of the invention.

I claim:

1. Facial Ironer apparatus comprising:

a housing;

a heating element having a base and a head and positioned in said housing;

electrical cord means connecting the apparatus to a source of electricity;

thermostatic switch means attached to said housing and interconnecting said cord means and said base of said heating element for keeping said heating element at a predetermined temperature;

a facial ironer separate from and demountably attached to said head of said heating element;

said facial ironer further comprising:

a soleplate having a top, a bottom and a slotted butt end;

said soleplate being sufficiently hollow for closely fitting over said head of said heating element through said slotted end;

said soleplate being heated by said heating element when said heating element is heated by the flow of electricity from said electrical cord means;

thermally insulated handle means for attachment to said top of said soleplate for manipulating said bottom of said ironer over the skin of the subject.

2. Facial Ironer apparatus comprising:

a housing having a partition for forming a first compartment and a second compartment;

an elongate metallic heating element having a base and a tapered head and positioned lengthwise in said housing and extending from either side of said partition and into both said compartments;

electrical cord means connecting the apparatus to a source of electricity;

thermostatic switch means positioned in said first compartment and interconnecting said cord means and said base of said heating element for keeping said heating element at a predetermined temperature;

a facial ironer separate from and demountably attached to said head of said heating element;

said facial ironer further comprising:

a blunt wedge shaped metallic soleplate having a top, bottom and a butt end;

said butt end having a receiving slot;

said soleplate being sufficiently hollow for closely fitting over said head of said heating element through said slot while resting said butt end against said partition;

said soleplate being heated by conductive heat from said heating element when said heating element is heated by the flow of electricity from said cord means;

thermally insulated handle means for attachment to said top of said soleplate for manipulating said bottom of said facial ironer over the prepared surface of the face area of the subject.

3. The apparatus as recited in claim 2 wherein said predetermined temperature is 96 degrees F.

4. The apparatus as recited in claim 2 further comprising a cover means for covering said second compartment and for securing said facial ironer when it is attached to said element head.

5. The apparatus as recited in claim 2 further comprising a light indicator means for indicating when said heating element is at the predetermined temperature.

6. Facial Ironer apparatus comprising:
   a housing;
   a heating element having a base and a head and positioned in said housing;
   electrical cord means connecting the apparatus to a source of electricity;
   rheostat switch means attached to said housing and interconnecting said cord means and said base of said heating element for adjusting the temperature of said heating element;
   a facial ironer separate from and demountably attached to said head of said heating element;
   said facial ironer further comprising:
      a soleplate having a top, a bottom and a slotted butt end;
      said soleplate being sufficiently hollow for closely fitting over said head of said heating element through said slotted end;
      said soleplate being heated by said heating element when said heating element is heated by the flow of electricity from said electrical cord means;
      thermally insulated handle means for attachment to said top of said soleplate for manipulating said bottom of said ironer over the skin of the subject.

7. Facial Ironer apparatus comprising:
   a housing having a partition for forming a first compartment and a second compartment;
   an elongate metallic heating element having a base and a tapered head and positioned lengthwise in said housing and extending from either side of said partition and into both said compartments;
   electrical cord means connecting the apparatus to a source of electricity;
   rheostat switch means positioned in said first compartment and interconnecting said cord means and said base of said heating element for adjusting the temperature of said heating element;
   a facial ironer separate from and demountably attached to said head of said heating element;
   said facial ironer further comprising:
      a blunt wedge shaped metallic soleplate having a top, a bottom and a butt end;
      said butt end having a receiving slot;
      said soleplate being sufficiently hollow for closely fitting over said head of said heating element through said slot while resting said butt end against said partition;
      said soleplate being heated by conductive heat from said heating element when said heating element is heated by the flow of electricity from said cord means;
      thermally insulated handle means for attachment to said top of said soleplate for manipulating said bottom of said facial ironer over the prepared surface of the face area of the subject.

* * * * *